US011484204B2

(12) United States Patent
Fitzgibbons et al.

(10) Patent No.: US 11,484,204 B2
(45) Date of Patent: Nov. 1, 2022

(54) ASSESSING SEPSIS RISK BASED ON DWELL TIMES OF INVASIVE DEVICES

(71) Applicant: Hill-Rom Services, Inc., Batesville, IN (US)

(72) Inventors: Stacey Ann Fitzgibbons, DeWitt, NY (US); Heather Dawn Kooiker, Caledonia, MI (US)

(73) Assignee: Hill-Rom Services, Inc., Batesville, IN (US)

( * ) Notice: Subject to any disclaimer, the term of this patent is extended or adjusted under 35 U.S.C. 154(b) by 303 days.

(21) Appl. No.: 16/917,561

(22) Filed: Jun. 30, 2020

(65) Prior Publication Data

US 2021/0000346 A1 Jan. 7, 2021

Related U.S. Application Data

(60) Provisional application No. 62/869,517, filed on Jul. 1, 2019.

(51) Int. Cl.
| | |
|---|---|
| *A61B 5/00* | (2006.01) |
| *A61B 34/00* | (2016.01) |
| *G16H 40/63* | (2018.01) |
| *A61B 90/98* | (2016.01) |
| *G06Q 10/06* | (2012.01) |

(52) U.S. Cl.
CPC ............ *A61B 5/0015* (2013.01); *A61B 5/746* (2013.01); *A61B 34/25* (2016.02); *A61B 90/98* (2016.02); *G06Q 10/0635* (2013.01); *G16H 40/63* (2018.01)

(58) Field of Classification Search
CPC .... A61B 5/0015; A61B 34/25; A61M 25/001; A61M 25/00; A61M 1/14
See application file for complete search history.

(56) References Cited

U.S. PATENT DOCUMENTS

| | | | |
|---|---|---|---|
| 7,988,633 B2 | 8/2011 | Hossack et al. | |
| 8,114,063 B2 | 2/2012 | Sacco et al. | |
| 9,642,967 B2 | 5/2017 | Ribble et al. | |
| 9,848,827 B1 | 12/2017 | LaBorde | |
| 2007/0085686 A1 | 4/2007 | Oz | |
| 2009/0209896 A1* | 8/2009 | Selevan | G04F 1/005 602/41 |
| 2013/0332184 A1 | 12/2013 | Burnham et al. | |

(Continued)

FOREIGN PATENT DOCUMENTS

WO WO2017055728 A2 4/2017

OTHER PUBLICATIONS

Rhee, et al., "Incidence and Trends of Sepsis in US Hospitals Using Clinical vs Claims Data, 2009-2014," JAMA, Sep. 2017;318(13):1241-1249.

*Primary Examiner* — Benyam Haile
(74) *Attorney, Agent, or Firm* — Lee & Hayes, P.C.

(57) ABSTRACT

Various methods, systems, and devices relate to identifying a sepsis risk of an individual based on a dwell time of an invasive device in the individual. An example method includes receiving, from multiple transceivers, location data indicating first signals transmitted between the multiple transceivers and a tag attached to the invasive device. A location of the invasive device can be identified based on the location data. The dwell time can be determined based on the location. In certain examples, a second signal indicating the sepsis risk can be generated.

20 Claims, 7 Drawing Sheets

(56) References Cited

U.S. PATENT DOCUMENTS

2017/0233798 A1* 8/2017 Neely .................. G01N 24/088
                                                    435/5
2018/0049923 A1    2/2018 Chen et al.
2019/0060126 A1    2/2019 Ribble et al.

* cited by examiner

ASSESSING SEPSIS RISK BASED ON DWELL TIMES OF INVASIVE DEVICES

CROSS-REFERENCE TO RELATED APPLICATION

This application claims the benefit of U.S. Provisional Application No. 62/869,517, filed on Jul. 1, 2019, which is hereby incorporated by reference in its entirety.

BACKGROUND

Sepsis can refer to a body's severe immune reaction to infectious agents circulating in the body's bloodstream. The immune reaction may cause the body to release immune chemicals throughout the bloodstream, which can result in inflammation, blood clots, and leaky blood vessels. The immune reaction may also cause one or more organs in the body to fail.

Hospitalized patients are at a unique risk for developing sepsis, and caring for patients with sepsis can significantly increase the cost of providing such care. The World Health Organization (WHO) estimates that 15% of hospitalized patients, worldwide, are septic. According to a retrospective study of U.S. hospitals in 2009-2014, 6% of hospitalized adults developed sepsis. Rhee C, et al., *Incidence and Trends of Sepsis in US Hospitals Using Clinical vs Claims Data, 2009-2014.* JAMA. 2017; 318(13):1241-1249. The average hospital stay for a patient with sepsis is about 15 days. Sepsis accounts for 11-12% of Intensive Care Unit (ICU) admissions. The total costs of admission and treatment of a patient with sepsis can cost $18,000 per stay in the U.S. An estimated total burden of sepsis treatment on the U.S. healthcare system is about $15.4 billion. As a result, public health organizations, hospitals, insurers, patients, and other health care organizations are interested in minimizing or eliminating sepsis incidence.

Unfortunately, assessing sepsis risk in individual patients can be difficult. Healthcare providers generally do not track the dwell times of invasive devices (e.g., catheters, bandages, etc.) in individual patients, and failure to track such dwell times can may significantly impact sepsis risk. Furthermore, care providers generally do not track how many invasive devices individual patients have been previously exposed to, which can also significantly impact sepsis risk. While such tracking may be desirable in a healthcare setting, known healthcare management applications and other tools typically are not configured to enable efficient, accurate, and user-friendly tracking of such sepsis risk factors. As a result, healthcare providers are often forced to be reactive to sepsis, rather than proactive in preventing sepsis.

SUMMARY

Various systems, methods, and devices for assessing sepsis risk in individual patients are provided herein. In example implementations, tags can be affixed to an invasive device and activated upon placement of the invasive device in a patient. The location of the tags (and the invasive device) can be identified using a Real Time Location System (RTLS). Using the activation and/or location of the tags, a dwell time of the invasive device can be determined.

In example implementations, the dwell time can be used to identify the patient's risk for developing sepsis. Based on the risk, various recommendations can be generated and provided to care providers for reducing the patient's risk for sepsis. In some examples, various implementations can be used to track sepsis incidence in a healthcare environment. The sepsis incidence can be used to generate a report

DESCRIPTION OF THE FIGURES

The following figures, which form a part of this disclosure, are illustrative of described technology and are not meant to limit the scope of the claims in any manner.

DETAILED DESCRIPTION

Figure 1:
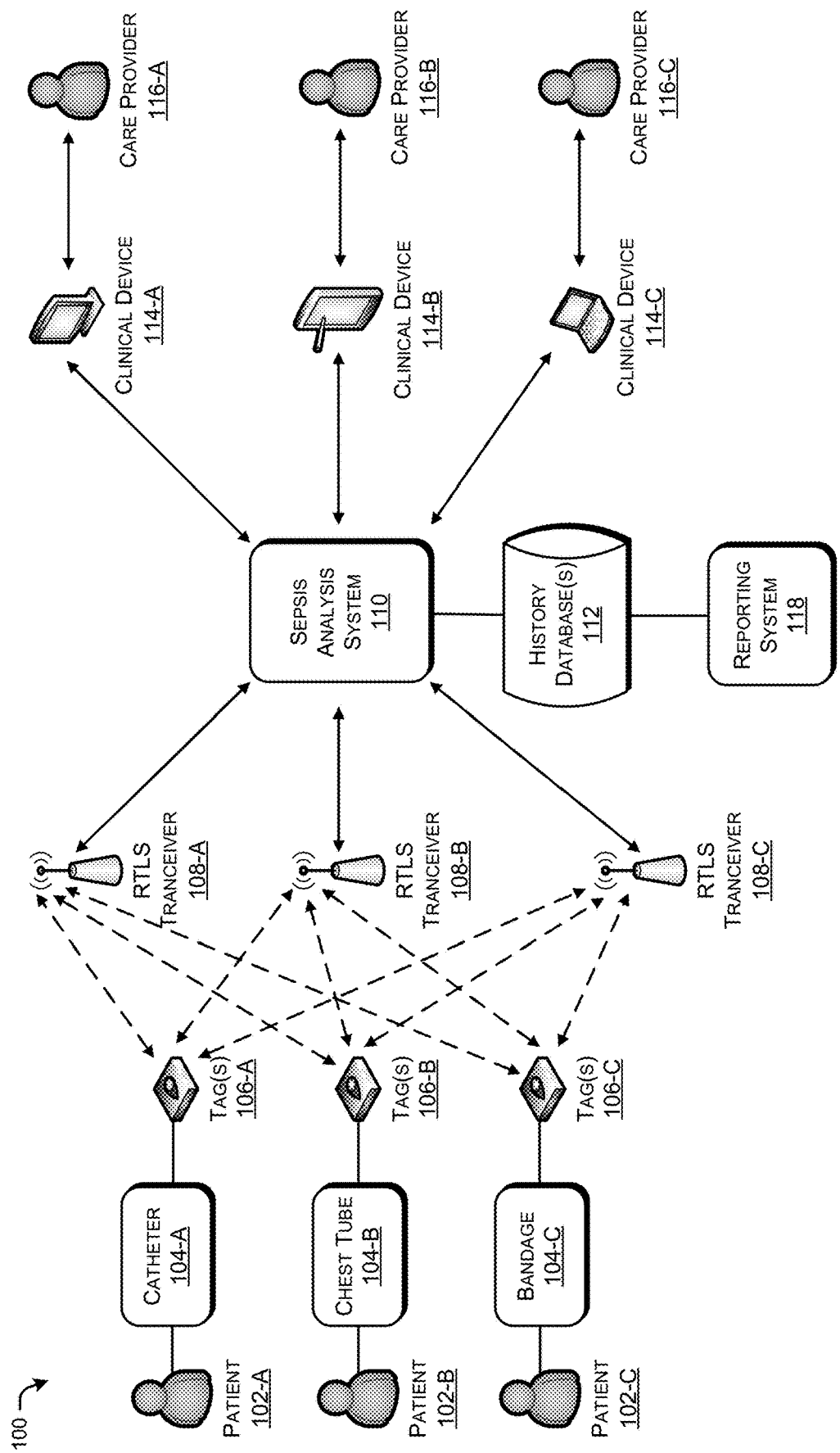
FIG. 1 illustrates an example environment for assessing sepsis risk based on dwell times of invasive devices.

Various implementations of the present disclosure will be described in detail with reference to the drawings, wherein like reference numerals present like parts and assemblies throughout the several views. Additionally, any examples set forth in this specification are not intended to be limiting and merely set forth some of the many possible implementations.

Example implementations relate to identifying an individual's risk of developing sepsis. The risk can be assessed based on a dwell time of an invasive device in the individual. The risk may also be assessed based on the dwell times of one or more invasive devices previously exposed to the individual.

As used herein, the term "sepsis risk" can refer to a likelihood that an individual will develop sepsis. For example, a sepsis risk can be represented by a percentage probability that that an individual will develop sepsis. In certain cases, a sepsis risk can also be associated with a confidence interval, may be limited to the likelihood that the individual will develop sepsis within a particular time period (e.g., one week), may be associated with a future treatment plan (e.g., the expected administration of antibiotics), or the like. By identifying an individual's risk for developing sepsis, care providers can tailor a care plan for the individual that can prevent the individual from developing sepsis.

As used herein, the term "individual" can refer to a human or a non-human animal being monitored. In some cases, an individual can be a patient in a healthcare facility. In particular instances, an individual can be a person monitored in a hospital setting, a ward (or floor) environment, an Intensive Care Unit (ICU), an assisted living facility, a hospice facility, or the like. In some instances, an individual can be anyone at risk for developing sepsis.

As used herein, the term "invasive device" can refer to any device that is introduced into a body or can otherwise exchange fluids with an environment in the body. In some examples, an invasive device can be inserted through a break in skin (e.g., through an incision), through an existing opening in the body (e.g., through a urethra), or the like. In some instances, an invasive device can be in physical contact with a break in skin (e.g., dressing a wound), in physical contact with an existing opening in the body, can exchange gasses with a device inserted through an opening in the body (e.g., gas supply of a ventilator), can exchange liquids with a device inserted through an opening in the body (e.g., contents of an IV), or the like. In some cases, an invasive device may be an implantable device. An individual's risk for sepsis may increase when the individual is exposed to an invasive device. The invasive device may introduce pathogens into the individual's bloodstream, lymphatic system, respiratory system, or the like. In some cases, the invasive device may trigger an immune response (e.g., a foreign body reaction) in the individual, regardless of whether the invasive device introduces pathogens to the individual. In some examples, an invasive device is a semi-permanent device, such as a surgical traction pin (e.g., associated with an open reduction and internal fixation procedure), a catheter (e.g., a dialysis catheter), a gastrostomy tube, a percutaneous endoscopic gastrostomy (PEG) tube, a nephrostomy tube, an endotracheal tube, a port for any of the tubes described herein, or the like.

As used herein, the term "dwell time" can refer to a time interval in which an invasive device is inserted in or is in physical contact with an individual. In some cases, a dwell time can be a time interval between a time at which the invasive device is placed into a body and a time at which the invasive device is removed from the body. In certain examples, in which an invasive device is currently placed in a body, a dwell time can be a time interval between a time at which the invasive device is placed and a current time.

In some implementations, an invasive device can be tracked with respect to an individual by attaching one or more tags to the invasive device and tracking the tags using a Real Time Location System (RTLS). For instance, the placement and/or removal of the invasive device can be automatically identified by tracking the location of tags attached to the invasive device. In some cases, the invasive device can be further tracked based on inputs to one or more clinical devices by care providers (e.g., nurses, physician assistants, physicians, or the like). For instance, a nurse can confirm whether an invasive device has been placed or removed by indicating the placement or removal on a user interface provided by a mobile phone, tablet, desktop computer, or the like.

As used herein, the term "tag" can refer to a physical device capable of storing information, transmitting information to a remote device, and/or receiving information from a remote device. A tag may be attached to a physical object (e.g., an invasive device). In various implementations, a tag can be passive, such that it collects energy from outside sources (e.g., radio waves) to power storage, data transmission, processing, or the like. In some implementations, a tag can be active, such that it may include a power source that can be used to power storage, data transmission, processing, or the like. Some examples of tags include Radio-Frequency Identification (RFID) tags, which can use electromagnetic signals to communicate with external devices. However, some tags can use non-radio-frequency electromagnetic signals, acoustic signals, or the like to communicate with external devices.

In certain implementations, the placement of an invasive device can be automatically identified in response to identifying that an initial signal has been received from one or more tags attached to the invasive device. As used herein, the term "initial signal" can refer to the first signal exchanged between at least one tag and at least one transceiver in a communication session. For example, an initial signal can refer to the first signal transmitted from a tag to a transceiver in an RTLS system upon activation of the tag. In some cases, activation can include activating power to circuitry in the tag, unwrapping the tag from packaging, or the like. In some implementations, activation can include a care provider indicating that that an invasive device attached to the tag has been placed in an individual via a user interface presented by a clinical device.

According to some implementations, the placement and/or removal of an invasive device can be identified based on the location of one or more tags attached to the invasive device. For instance, the placement of the invasive device can be identified in response to identifying that the tag(s) are within a predetermined distance of a tag associated with an individual (e.g., a tag worn by the individual, a tag attached to a medical device utilized to treat the individual, etc.) or within an area associated with the individual (e.g., a hospital room assigned to the individual). In some examples, the removal of an invasive device can be automatically identified in response to identifying that one or more tags attached to the invasive device are located in a discard area. As used herein, the term "discard area" can refer to a physical area and/or volume where an invasive device can be placed after use. In some implementations, a discard area can be a biological waste container, an autoclave, a waste bag, or the like. In some cases, a discard area can be predefined by the system, such that a predefined area or volume of a building being monitored can be defined as a discard area. In certain cases, the discard area can be defined by one or more tags. For example, a waste container can be attached to one or more tags, such that the waste container can be defined as a discard area even if the waste container is moved to different areas of a hospital.

In some implementations, the sepsis risk of an individual can be identified using at least one trained neural network. As used herein, the term "neural network" can refer to a computer system that is configured to learn to perform tasks. In some implementations, a neural network learns how to perform tasks by undergoing a training protocol, in which parameters of the neural network are optimized based on sample inputs and sample outputs. After the neural network is trained, the neural network may be configured to generate new outputs based on new inputs. According to some implementations, an input to the neural network can include at least one of a dwell time of an invasive device currently exposed to an individual, dwell time(s) of any invasive device previously exposed to the individual, medical history information associated with the individual, or the like. The neural network can be trained using various features of other individuals who may or may not have developed sepsis.

Various implementations of the present disclosure will now be described with reference to the accompanying figures.

FIG. 1 illustrates an example environment 100 for assessing sepsis risk based on dwell times of invasive devices. In some implementations, the environment 100 can be implemented in a healthcare facility, such as a hospital, health clinic, hospice, assisted living facility, extended care facility, or the like. The environment 100 can include multiple patients 102-A to 102-C who may be at risk for developing sepsis. In some cases, the patients 102-A to 102-C can include individuals located in the same healthcare facility.

Each of the patients 102-A to 102-C may be exposed to at least one invasive device 104-A to 104-C. For instance, a catheter 104-A may be placed in patient 102-A, a chest tube may be placed in patient 102-B, and a bandage 104-C may be placed on a wound of patient 102-C. The invasive devices 104-A to 104-C may affect the patients' 102-A to 102-C respective risks for developing sepsis. In some cases, the dwell times of the invasive devices 104-A to 104-C in the patients 102-A to 102-C may affect the patients' 102-A to 102-C risks for developing sepsis.

In some implementations, each of the tags 106-A to 106-C may be attached to invasive devices 104-A to 104-C. For instance, tag(s) 106-A may be attached to the catheter 104-A, tag(s) 106-B may be attached to the chest tube 104-B, and tag(s) 106-C may be attached to the bandage 104-C. The tags 106-A to 106-C can be attached to the invasive devices 104-A to 104-C by various techniques. For instance, the tags 106-A to 106-C may be attached to the invasive devices 104-A to 104-C via an adhesive, such as an acrylic adhesive, a rubber adhesive, or the like. In some cases, the tags 106-A to 106-C can be physically integrated with the invasive devices 104-A to 104-C. For example, the tags 106-A to 106-C can be cast in a polymer coating of the invasive devices 104-A to 104-C.

The tags 106-A to 106-C may be configured to transmit signals to RTLS transceivers 108-A to 108-C. In some implementations, the signals may be wireless signals transmitted over one or more wireless channels. The signals can be electromagnetic signals, ultrasonic signals, subsonic signals, or the like. According to some implementations, the signals can encode data by emitting signals in one or more frequencies. For instance, the signals can transmit data via at least one frequency using Frequency Shift Keying (FSK), Orthogonal Frequency Division Multiplexing (OFDM), or the like.

In certain cases, the signals may identify the tags 106-A to 106-C that originate the signals. For instance, the signals may encode identifiers of the tags 106-A to 106-C. In some cases, the tags 106-A to 106-C may be further configured to receive signals from the RTLS transceivers 108-A to 108-C. According to some examples, the tags 106-A to 106-C may be configured to transmit signals to the RTLS transceivers 108-A to 108-C in response to receiving signals from the RTLS-transceivers 108-A to 108-C.

In example implementations, the RTLS transceivers 108-A to 108-C may be located in fixed positions within or around the healthcare facility. The RTLS transceivers 108-A to 108-C may identify at least one of a time at which each signal is received, a direction from which each signal is received, or the like. Each of the RTLS transceivers 108-A to 108-C may report various information about the signals it receives from the tags 106-A to 106-C (e.g., the originating tag, the identity and/or of the RTLS transceiver, the time at which a signal was received, the direction from which the signal was received, etc.) to a sepsis analysis system 110.

The transmission of the signals from the tags 106-A to 106-C to the RTLS transceivers 108-A to 108-C may indicate the physical locations of the tags 106-A to 106-C. In some cases, the locations of the tags may be determined by the RTLS transceivers 108-A to 108-C and/or the sepsis analysis system 110 in communication with the RTLS transceivers 108-A to 108-C. In example implementations, the locations of the tags 106-A to 106-C may be determined using trilateration, multilateration, triangulation, or the like.

For example, tag 106-A may transmit signals that are received by the RTLS transceivers 108-A to 108-C. The signals may indicate an identity of the tag 106-A, as well as a transmission time of the signals, at which the tag 106-A has transmitted the signals. The RTLS transceivers 108-A to 108-C may identify reception times of the signals, at which the RTLS transceivers 108-A to 108-C receive the signals from the tag 106-A. A velocity of the signals may be predetermined (e.g., the speed of sound for subsonic or ultrasonic signals, the speed of light for electromagnetic signals, etc.). Accordingly, the RTLS transceivers 108-A to 108-C and/or the sepsis analysis system 110 may determine the distances between the tag 106-A and the respective RTLS transceivers 108-A to 108-C by multiplying the velocity of the signals by the time intervals defined between the transmission time and the reception times. Once the distances are determined, the location of the tag 106-A may be derived via trilateration or multilateration.

In some instances, the RTLS transceivers 108-A to 108-C may receive signals from the tag 106-A and may identify directions (i.e., angles) at which the signals are received. Based on the directions and the known locations of the RTLS transceivers 108-A to 108-C, the location of the tag 106-A may be derived via triangulation.

According to various implementations, the sepsis analysis system 110 may be configured to identify dwell times of the invasive devices 104-A to 104-C. In some examples, the sepsis analysis system 110 may identify a time (e.g., a "placement time") at which one of the invasive devices 104-A to 104-C is placed in the corresponding one of the patients 102-A to 102-C. According to some example implementations, the placement time can be determined based on an activation of the tags 106-A to 106-C. For instance, the tag(s) 106-A may be activated by a clinician when the catheter 104-A is placed in the patient 102-A by the clinician. In some cases, the tags 106-A to 106-C can be activated by unwrapping the tags 106-A to 106-C from packaging, connecting an electronic circuit within the tags 106-A to 106-C, powering the tags 106-A to 106-C on, or the like. In some cases, the clinician activating a particular one of the tags 106-A to 106-C may log on to an online account and use the account to indicate that the tag has been activated.

In some example implementations, an initial signal transmitted from the tags 106-A to 106-C to the RTLS transceivers 108-A to 108-C can be used to identify when the tags 106-A to 106-C have been placed. The initial signal may carry data indicating that it is an initial signal. In some cases, the initial signal can be identified by identifying that it is the first signal that the RTLS transceivers 108-A to 108-C has received from a given one of the tags 106-A to 106-C.

In some cases, the signals transmitted from the tags 106-A to 106-C to the RTLS transceivers 108-A to 108-C may include timestamps, tag identifiers, or other forms of metadata that can be used to identify the transmitting tags 106-A to 106-C and/or information that can be used to derive the angles or times of flight of the signals. For instance, a signal transmitted from the tag(s) 106-A to the RTLS transceiver 108-A may encode a time at which the signal has been transmitted and the RTLS transceiver 108-A may identify a time at which the signal is received. The sepsis analysis system 110 may be able to identify the relative location of the tag 106-A with respect to the RTLS transceiver 108-A based on these times.

According to some examples, the sepsis analysis system 110 may be able to identify the placement times of the invasive devices 104-A to 104-C based on the location of the tags 106-A to 106-C. For example, when the tag(s) 106-A is determined to be in a location that is at least in close proximity to the patient 102-A (e.g., within a threshold distance of a hospital bed associated with the patient 102-A, within a room utilized by the patient 102-A, or the like), the sepsis analysis system 110 may identify that the catheter 104-A has been placed in the patient 102-A.

In some implementations, the sepsis analysis system 110 may identify a time (e.g., a "removal time") at which one of the invasive devices 104-A to 104-C is removed from the corresponding one of the patients 102-A to 102-C. In certain examples, the removal time can be identified based on a deactivation of the tags 106-A to 106-C. For instance, the tag(s) 106-C may be deactivated by a clinician when the bandage 104-C is removed from the patient 102-C. The tags 106-A to 106-C can be deactivated by being wrapped in shielding, disconnecting an electric circuit within the tags 106-A to 106-C, powering the tags 106-A to 106-C off, or the like. In some cases, the clinician activating a particular one of the tags 106-A to 106-C may log on to an online account and use the account to indicate that the tag has been deactivated.

According to some examples, the removal times of the invasive devices 104-A to 104-C can be identified based on the locations of the tags 106-A to 106-C. In example implementations, the removal time of a particular one of the devices 104-A to 104-C can be identified in response to identifying that a corresponding one of the tags 106-A to 106-C is located in a predetermined discard area (e.g., a wastebasket, an autoclave, a sharps container, etc.), is greater than a threshold distance of the corresponding one of the patients 102-A to 102-C, or is located outside of a room accommodating any of the patients 102-A to 102-C.

The dwell times of any one of the invasive devices 104-A to 104-C can be identified based on at least one of the placement time or the removal time of the corresponding device 104-A to 104-C. For example, the dwell time can be identified as the time interval between the placement time and the removal time. In some cases, wherein the invasive device 104-A to 104-C has not been removed, the dwell time can be identified as the time interval between the placement time and a current time.

In various implementations, the sepsis analysis system 110 can identify a sepsis risk of each of the patients 102-A to 102-C based on the dwell times of invasive devices 104-A to 104-C. For instance, the dwell times of invasive devices may correlate to a higher risk of developing sepsis. In some cases, the sepsis analysis system 110 may access at least one history database 112 to identify health records about the patients 102-A to 102-C. Various data in the health records can be used to identify the sepsis risk of the patients 102-A to 102-C. For example, the number of invasive devices previously placed in patient 102-A may impact patient's 102-A risk for developing sepsis. In some instances, the dwell times of invasive devices previously placed in patient 102-B may impact patient's 102-B risk for developing sepsis. According to some cases, a drug previously administered to patient 102-C (e.g., an antibiotic) may impact patient's 102-C risk for developing sepsis. The health records may include information such as a number of previously placed invasive devices, dwell times of previously placed invasive devices, prescriptions administered, diseases, travel histories, or the like, of the patients 102-A to 102-C. The sepsis analysis system 110 may input various factors associated with the dwell times of the invasive devices 104-A to 104-C and/or the health records of the patients 102-A to 102-C may into a model (e.g., a trained neural network) to determine the sepsis risks of the patients 102-A to 102-C. In addition, the sepsis analysis system 110 may update the sepsis risks of the patients 102-A to 102-C in real time, in response to changes in the dwell times of the invasive devices 104-A to 104-C and/or the health records of the patients 102-A to 102-C.

In some examples, the sepsis analysis system 110 can identify the sepsis risk of any of the patients 102-A to 102-C based on the identification of maintenance care activities on the invasive devices 104-A to 104-C. For instance, the invasive device 104-A may be a semi-permanent invasive device (e.g., a surgical traction pin, a dialysis catheter, a gastrostomy tube, a PEG tube, a nephrostomy tube, an endotracheal tube, a port for any of the before-mentioned tubes, or the like). As a semi-permanent invasive device, the invasive device 104-A may be designed to be in contact with the patient 102-A for an extended period of time (e.g., at least one week, at least one month, at least a year, no more than 5 years, or the like). To reduce the patient's 102-A risk of developing sepsis, at least one maintenance activity may be performed on the invasive device 104-A during the dwell time of the first invasive device 104-A. A maintenance activity can include, for instance, cleaning a site of the invasive device 104-A (e.g., cleaning an exit site of a dialysis catheter). The sepsis analysis system 110 may identify the performance of a maintenance activity on the invasive device 104-A and calculate the sepsis risk based on the maintenance activity. For instance, a maintenance activity performed on the invasive device 104-A may decrease the sepsis risk of the patient 102-A. In some cases, missing a scheduled maintenance activity (e.g., an activity expected to be performed at a particular time or at a particular frequency during the dwell time of the invasive device 104-A) may increase the sepsis risk of the f patient 102-A.

The sepsis analysis system 110 may also identify a recommendation associated with the care of the patients 102-A to 102-C based on at least one of the dwell times, the sepsis risks, or the health records. For example, the sepsis analysis system 110 may identify a recommendation specifying at least one of when one of the invasive devices 104-A to 104-C should be removed, whether future placement of invasive devices should be avoided for any of the patients 102-A to 102-C, whether additional infection control procedures should be implemented for any of the patients 102-A to 102-C, whether any of the patients 102-A to 102-C should be treated prophylactically to avoid sepsis, or the like.

The sepsis analysis system 110 may cause any of clinical devices 114-A to 114-C to output the sepsis risk and/or the recommendation. The clinical devices 114-A to 114-C may be configured to receive the sepsis risk and/or the recommendation from the sepsis system 110 via one or more wired and/or wireless networks. The clinical devices 114-A to 114-C can include computers, tablets, laptops, mobile devices, or any other type of electronic device configured to communicate with the sepsis system and to output information.

In some cases, care providers 116-A to 116-C may learn about the sepsis risk and/or the recommendation output by the clinical devices 114-A to 114-C. The care providers 116-A to 116-C may perform various tasks associated with the care of the patients 102-A to 102-C based on the sepsis risk and/or the recommendation. In some implementations, the care providers 116-A to 116-C perform maintenance activities on the invasive devices 104-A to 104-C. In some cases, the sepsis analysis system 110 may identify the performance of a maintenance activity by receiving a notification, from any one of the clinical devices 114-A to 114-C operated by the care providers 116-A to 116-C, indicating that the maintenance activity has been performed. For instance, the first care provider 116-A may perform a maintenance activity on the first invasive device 104-A, and may input an indication of the maintenance activity in the first clinical device 114-A, which could, in turn, notify the sepsis analysis system 110. Thus, the sepsis analysis system 110 may determine whether the maintenance activity has been performed and adjust the sepsis risk of the first patient 102-A accordingly.

According to example implementations, the sepsis analysis system 110 can further cause storage of the sepsis risk and/or the recommendation in the history database(s) 112. Accordingly, an up-to-date record of the sepsis risk and/or applicable clinical plans can be stored in the history database(s) 112. In some cases, the history database(s) 112 may further store indications of various patients who have developed sepsis in the healthcare facility. In some cases, the sepsis analysis system 110 can access the history database(s) 112 to identify various information that the sepsis analysis system 110 can use to identify the sepsis risk. For instance, the history database(s) 112 may store various health record information associated with the patients 102-A to 102-C that can be relevant to their risks of developing sepsis. In some cases, the history database(s) 112 may further store health information of various patients who have been placed with invasive device and/or may have developed sepsis (e.g., in the healthcare facility). According to some example implementations, the sepsis analysis system 110 may utilize this information to draw general conclusions (e.g., correlations) between dwell times and sepsis risk, which the sepsis analysis system 110 can use for identifying the sepsis risks of the patients 102-A to 102-C.

A reporting system 118 may be configured to generate reports about sepsis risk, sepsis incidence, and the like, of multiple patients in the healthcare facility. For instance, the reporting system 118 can generate a report detailing care of patients who developed sepsis in the healthcare facility. In some cases, the reporting system 118 can further identify trends associated with the sepsis risks, recommendations, and development of sepsis by the patients.

Figure 2:
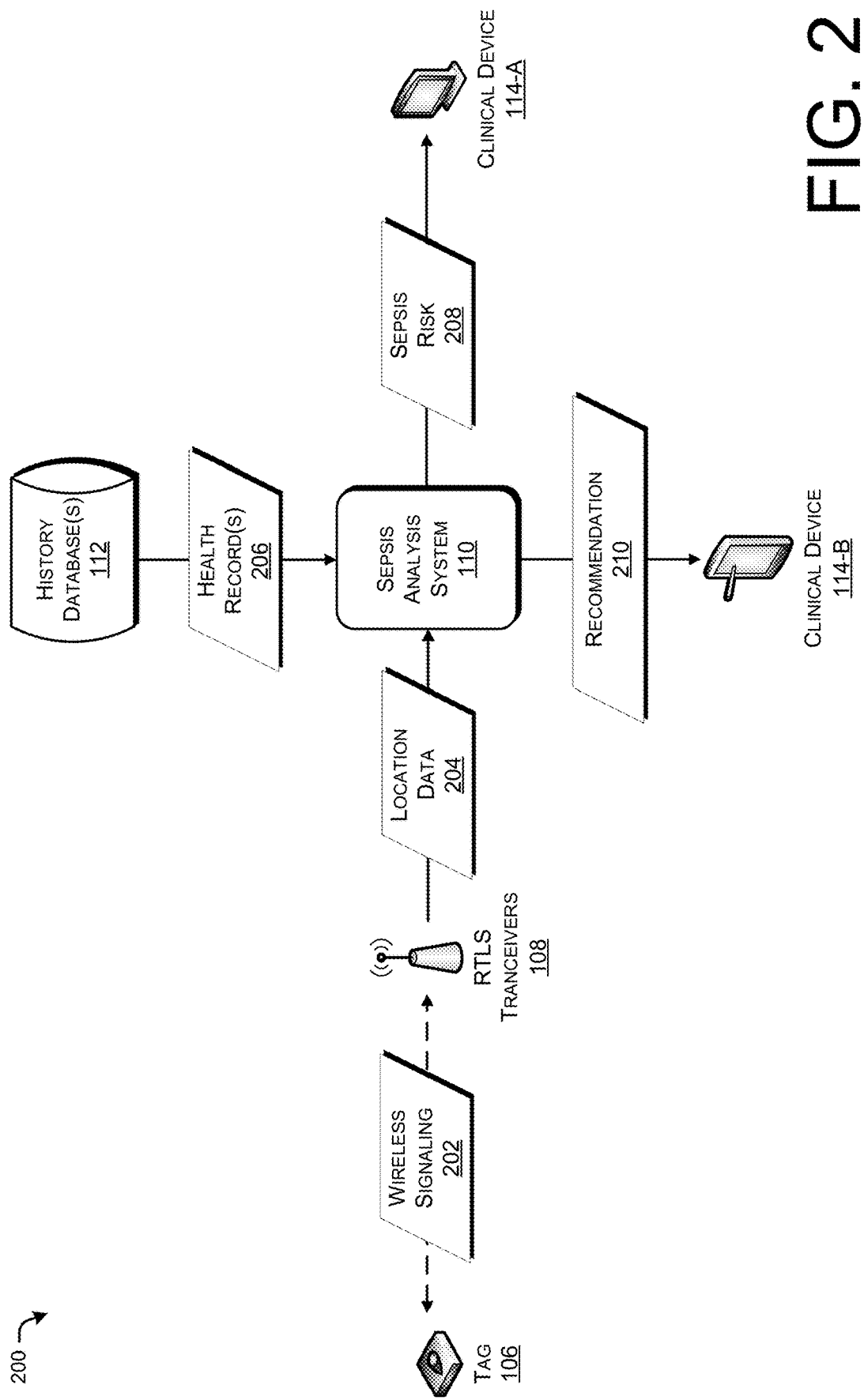
FIG. 2 illustrates example signaling for assessing sepsis risk based on dwell times of invasive devices.

FIG. 2 illustrates example signaling 200 for assessing sepsis risk based on dwell times of invasive devices. The signaling 200 can involve various components of the environment 100 described above with reference to FIG. 1, such as a tag 106, RTLS transceivers 108, a sepsis analysis system 110, at least one history database 112, and clinical devices 114-A and 114-B, by way of example.

The tag 106 may be attached to an invasive device that may be placed in and/or removed from an individual, such as a patient. The tag 106 may exchange wireless signaling 202 with the RTLS transceivers 108. In some implementations, the wireless signaling 202 may exclusively include transmissions from the tag 106 to the RTLS transceivers 108, and the RTLS transceivers 108 may not transmit wireless signals to the tag 106.

The wireless signaling 202 may be transmitted over one or more wireless channels. In some cases, the wireless signaling 202 may encode data in the one or more wireless channels using various techniques, such as frequency shift keying (FSK), orthogonal frequency division multiplexing (OFDM), or the like. In some cases, the wireless signaling 202 can include at least one of electromagnetic signals (e.g., radio frequency signaling), sound signals (e.g., ultrasonic and/or subsonic signals), or the like.

The data encoded in the wireless signaling 202 can identify the tag 106, in some example implementations. For instance, the data can indicate an identifier of the tag 106. In some examples, the tag 106 may be associated with a unique ID code (e.g., a unique string) that can be used to distinguish the tag 106 from other tags that may be transmitting signals to the RTLS transceivers 108. In some cases, the ID code may be indicated in a header of a data packet transmitted from the tag 106 to the RTLS transceivers 108 in the wireless signaling 202. In some cases, the identifier of the tag 106 can be used to identify an ID of the invasive device attached to the tag 106, an ID of the patient in which the invasive device is placed, an ID of a hospital bed assigned to the patient, a room assigned to the patient in the healthcare facility, etc. For example, correlations between the identifier of the tag 106 and information associated with the patient can be stored, or at least accessed (e.g., in the history database(s) 112), by the sepsis analysis system 110.

In some cases, the data encoded in the wireless signaling 202 can identify a transmission time of the wireless signaling 202. For instance, the tag 106 may generate a data packet to include a transmission time of the data packet to the RTLS transceivers 108. In some cases, the tag 106 may automatically transmit data packets at a predictable time (e.g., periodically), such that the transmission time of a particular data packet can be predicted regardless of the content of the data packet.

The RTLS transceivers 108 may generate location data 204 in response to the wireless signaling 202. The RTLS transceivers 108 may further transmit the location data 204 to the sepsis analysis system 110. The location data 204 may indicate the ID code of the tag 106. In some cases, the location data 204 may include at least one of the transmission times of the wireless signaling 202, the reception times of the wireless signaling 202, round trip times (RTTs) of the wireless signaling 202 (e.g., a time between transmission of a request from an RTLS transceiver 108 and a response to the request from the tag 106), the reception angles of the wireless signaling 202, or the like.

The sepsis analysis system 110 can identify the location of the tag 106 based on the location data 204. In example implementations, the sepsis analysis system 110 may identify the location of the tag 106 by performing trilateration, multilateration, triangulation, or the like. For example, the sepsis analysis system 110 can determine time lags of the wireless signaling 202 between the tag 106 and the respective RTLS transceivers 108 based on the transmission times and the reception times (or based on a one-way transmission time derived from a RTT), and can determine the distances between the tag 106 and the RTLS transceivers 108 by multiplying the time lags by the velocity of the wireless signaling 202.

In various implementations, the sepsis analysis system 110 can identify a dwell time of the invasive device attached to the tag 106 based on the location data 204. In some instances, the sepsis analysis system 110 can identify the placement of the invasive device and/or the removal of the invasive device based on the location data 204. For example, the sepsis analysis system 110 may determine that the invasive device has been placed in the patient in response to identifying that the location of the tag 106 is within a predetermined distance of the patient. The location of the patient may be identified by identifying the location of another tag associated with the patient (e.g., via the RTLS transceivers 108), such as a tag on a hospital bracelet, a tag worn on a lanyard around the patient's neck, or the like. In some cases, the placement of the invasive device can be determined in response to identifying that the location of the tag 106 is within a predetermined distance of a tag attached to an object associated with the patient, such as a hospital bed, a ventilator device, a pulse oximeter device, a heart rate monitor, or some other invasive device currently placed in the patient. In some examples, the placement of the invasive device can be determined in response to identifying that the location of the tag 106 is within a predetermined area associated with the patient, such as within a room utilized by the patient, a floor on which the patient is being treated, a unit in which the patient is being treated, or the like.

According to some examples, the sepsis analysis system 110 may identify that the invasive device has been removed from the patient at least partly in response to identifying that that the invasive device has been previously placed in the patient. In some examples, the sepsis analysis system 110 may determine that the invasive device has been removed upon identifying that the tag 106 is greater than a predetermined distance away from a tag associated with the patient, the object associated with the patient, or the predetermined area associated with the patient.

In some example implementations, the sepsis analysis system 110 may identify that the invasive device has been removed in response to determining that the tag 106 is located within a discard area. The discard area may be a place where care providers dispose of invasive devices. According to various examples, the discard area can be at least one of a wastebasket, a sharps container, an autoclave, a biohazard bag, a waste collection area, or the like. In some cases, the discard area can be defined by one or more tags whose location can be tracked by the sepsis analysis system 110. Accordingly, if the discard area moves (e.g., a sharps container is moved from one area to another area in a room), the sepsis analysis system 110 can track its location.

According to some examples, the sepsis analysis system 110 can identify the dwell time based a time at which the invasive device is placed and/or a time at which the invasive device is removed. For example, the dwell time may be defined as a time interval between the placement time and the removal time. In some examples, wherein the device has not been removed, the dwell time may be defined as a time interval between the placement time and a current time. In some examples, the sepsis analysis system 110 can rely at least partly on other information to identify the dwell time. For instance, the sepsis analysis system 110 may identify that an invasive device attached to the tag 106 has been placed in response to identifying that a care provider has indicated the placement of the invasive device in the patient's health record.

The sepsis analysis system 110 may be configured to identify a sepsis risk of the patient. The sepsis analysis system 110 may transmit the sepsis risk 208 to clinical device 114-A. The clinical device 114-A may, in turn, output the sepsis risk 208 to a care provider. Accordingly, the care provider may be able to make decisions about the patient's care plan based on the patient's risk of developing sepsis.

In various implementations, the sepsis analysis system may use the dwell time of the invasive device to identify the patient's sepsis risk 208. For instance, the patient's sepsis risk 208 may increase as the dwell time increases. In some cases, the sepsis analysis system 110 may be configured to identify the sepsis risk 208 based on one or more health records 206 associated with the patient. The sepsis analysis system 110 may receive the health record(s) 206 from the history database(s) 112, which may store the health record(s) 206 of the patient along with additional health-related information about the patient and/or other patients who have been monitored in the healthcare facility.

In some examples, the health record(s) 206 may include information indicating previous invasive devices exposed to the patient. For instance, the health record(s) 206 can indicate the number of invasive devices previously placed in the patient, the dwell times of the previously placed invasive devices, and the like. The patient's sepsis risk 208 may increase as the number of invasive devices previously placed in the patient increases and/or as the dwell times of the previously placed invasive devices also increases. In some cases, the health record(s) 206 can identify a frequency in which the invasive devices were previously placed. For example, the dwell times of devices placed in the patient over a month prior may have a relatively insignificant impact on the patient's sepsis risk 208, whereas the dwell times of devices placed in the patient less than a week prior may have a relatively significant impact on the patient's sepsis risk 208. According to some examples, the health record(s) 206 may identify the types of the previously placed invasive devices. For instance, a catheter may have a greater impact on the patient's sepsis risk 208 than a wound dressing.

In some example implementations, the health record(s) 206 may identify other types of information that can be used by the sepsis analysis system 110 to identify the sepsis risk 208. For example, the health record(s) 206 may indicate health conditions (e.g., HIV status) of the patient that indicate the patient is immunocompromised, and therefore at a greater risk for developing sepsis. The health record(s) 206 may indicate whether the patient has been diagnosed with an infection by a care provider, which may increase the patient's sepsis risk 208. In some cases, the health record(s) 206 may indicate whether the patient has been administered any therapies that may be relevant to the patient's sepsis risk 208. For example, a patient who has been administered antibiotics may have a lower sepsis risk 208 than a patient who has not been administered antibiotics.

In some cases, the sepsis analysis system 110 can use a trained neural network to identify the sepsis risk 208. For example, the sepsis analysis system 110 may input at least one of the location of the tag 106, the dwell time of the invasive device, or the health record(s) 206 into the trained neural network, and the trained neural network may output the sepsis risk 208. The neural network can be trained according to various previously observed patient data and sepsis outcome data.

According to various implementations, the sepsis analysis system 110 may also identify a recommendation 210 associated with the patient. The sepsis analysis system 110 may transmit the recommendation 210 to clinical device 114-B, in some cases. In turn, clinical device 114-B may output the recommendation 210 to a care provider. The care provider may use the recommendation 210 to identify actions to take with regard to the care of the patient.

In some cases, the sepsis analysis system 110 may identify the recommendation 210 based on the dwell time of the invasive device. For example, in response to identifying that the invasive device is currently placed in the patient and that the dwell time of the invasive device exceeds a threshold (e.g., 8 hours, or some other threshold according to manufacturer instructions associated with the invasive device), the sepsis analysis system 110 may generate the recommendation 210 to indicate that the invasive device should be removed immediately or within a particular time frame (e.g., within the hour).

In some examples, the sepsis analysis system 110 may identify the recommendation 210 based on the sepsis risk 208 of the patient. The recommendation 210 may include a recommendation for additional monitoring (e.g., more frequent vital sign monitoring) of the patient and/or therapies (e.g., prophylactic antibiotics) to be administered to the patient based on the sepsis risk 208. In some cases, the sepsis analysis system 110 can identify that additional monitoring and/or therapies should be provided to the patient in response to identifying that the sepsis risk is above a particular threshold (e.g., the patient has a greater than 50% risk of developing sepsis).

In certain implementations, the sepsis analysis system 110 can use a trained neural network to generate the recommendation 210. For instance, the sepsis analysis system 110 can input at least one of the location of the tag 106, the dwell time of the invasive device, the health record(s) 206, or the sepsis risk 208 into a trained neural network, and, in response, the trained neural network may output the recommendation 210. The neural network may be trained with various patient data and previously observed health outcomes.

Figure 3:
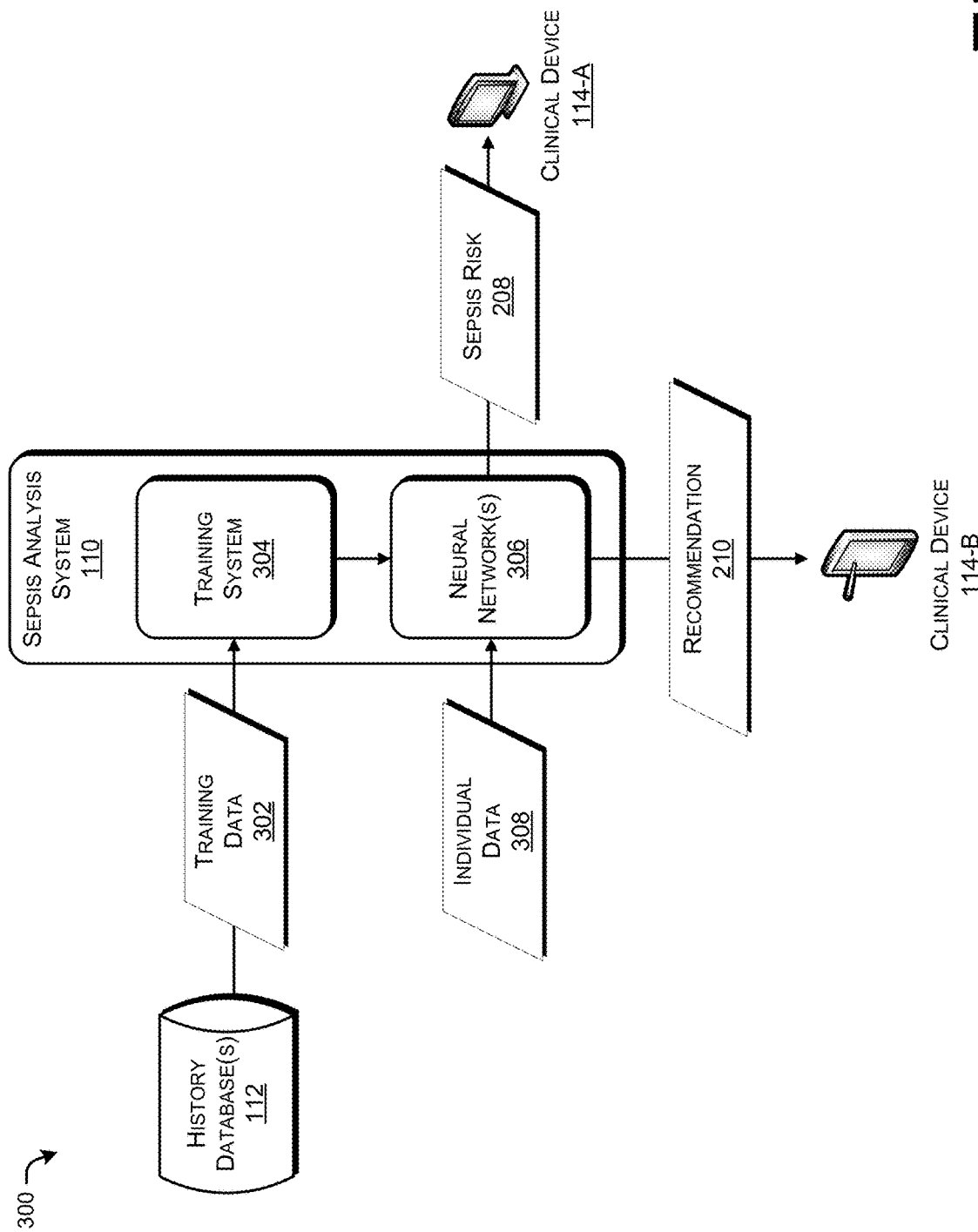
FIG. 3 illustrates an example signaling for assessing sepsis risk using machine learning.

FIG. 3 illustrates example signaling 300 for assessing sepsis risk using machine learning. The signaling 300 can involve various components of the environment 100 described above with reference to FIG. 1, such as a sepsis analysis system 110, at least one history database 112, and clinical devices 114-A and 114-B, by way of example. Further, the signaling 300 may involve various components of the signaling 200 described above with reference to FIG. 2, such as the sepsis risk 208 and the recommendation 210.

The history database(s) 112 may provide training data 302 to a training system 304 in the sepsis analysis system 110. The training data 302 may include information about various patients, such as patients previously treated in the healthcare facility, patients previously treated in similar healthcare facilities, or the like. The various patients may include patients with various demographics, such as patients with different genders, races, educational attainment, body mass indices (BMIs), preexisting conditions, or the like. In some instances, the training data 302 may represent information about a diverse set of patients.

The training data 302 may include information about invasive devices placed in the various patients. For example, the training data 302 may indicate what types of invasive devices were placed in the various patients, a frequency of invasive device placement, a number of the invasive devices placed in the various patients, dwell times of the invasive devices, where the patients were located when the invasive devices were placed, or the like. The training data 302 may further include sepsis outcomes about the various patients. For example, the training data 302 may indicate whether the various patients developed sepsis, times at which the patients developed sepsis, or the like. In some cases, the training data 302 can include other health-related information about the patients. For instance, the training data 302 may indicate whether any of the various patients were immunocompromised, whether any of the patients were administered therapies, whether any of the patients previously experienced sepsis, or the like.

Within the sepsis analysis system 110, the training system 304 may train at least one artificial neural network 306 based on the training data 302. In some example implementations, the neural network(s) 306 may be trained to output the sepsis risk 208 and/or the recommendation 210 based on individual data 308, which may correspond to a new patient whose information is excluded from the training data 302. The neural network(s) 306 may include multiple layers, wherein each of the layers includes multiple neurons (also referred to as "nodes"). Each of the neurons may be designed to perform a function (e.g., multiplication, convolution, or the like) on an input according to one or more weights (e.g., filters, constants, or the like).

The training system 304 may be configured to optimize the weights in the neurons of the neural network(s) 306, so that the neural network(s) 306 are designed to output information associated with the sepsis outcomes in the training data 302 in response to receiving input associated with the training data 302. In some cases, the training system 304 can optimize the weights by repeating a propagation phase and a weight update phase. In the propagation phase, the training system 304 may initialize the weights of the neural network(s) 306 and input a first portion of the training data 302 corresponding to conditions that may affect various patients' risks of developing sepsis. The first portion can include data representing at least one of the number of invasive devices placed in the various patients, the dwell times of the invasive devices, treatments performed on the various patients, medical histories of the various patients, and the like, into the neural network(s) 306. The training system 304 can compare the resultant output from the neural network(s) 306 to an ideal output based on a second portion of the training data 302 corresponding to outcomes of the various patients. The second portion can include data representing at least one of whether the various patients developed sepsis or treatments that affected (e.g., cured or prevented) any cases of sepsis in the various patients. In some cases, the training system 304 may calculate an error between the output of the neural network(s) 306 and an ideal output (e.g., a true sepsis risk) based on second portion of the training data 302. In the weight update phase, the training system 304 can modify the previous weights of the neural network(s) 306 based on the error. The propagation and weight update phases can be repeated until an acceptable error (e.g., below a particular threshold, or a minimum error among errors produced by a number of propagation and weight update cycles) between the first portion and the ideal output is achieved. In certain implementations, the ideal output can correspond to a predicted sepsis risk of the various patients and/or an ideal care plan for the various patients based on the outcomes of the various patients. In some cases, ideal output may by performing predictive inference second portion of the training data 302 using Bayesian prediction.

Once trained, the neural network(s) 306 may receive individual data 308. The individual data 308 may include various health-related information about a particular individual that may be relevant to the individual's risk for developing sepsis. Some examples of the individual data 308 may include location data (e.g., location data 204) and/or health record(s) (e.g., health record(s) 206) corresponding to a particular individual.

In response to receiving the individual data 308, the neural network(s) 306 may output the sepsis risk 208 and/or the recommendation 210. The sepsis risk 208 may correspond to a predictive inference of the individual's risk for developing sepsis. The recommendation 210 may correspond to a predictive inference of the ideal care plan to prevent the individual's risk of developing sepsis. An ideal care plan may correspond to a care plan that is predicted to decrease the individual's risk for developing sepsis below a particular threshold (e.g., below 10%). In some cases, the recommendation 210 can include a care plan selected among multiple care plans based on the cost of the care plan (e.g., the least expensive acceptable care plan), possible side-effects (e.g., an acceptable care plan with the least severe expected side effects), etc.

Figure 4:
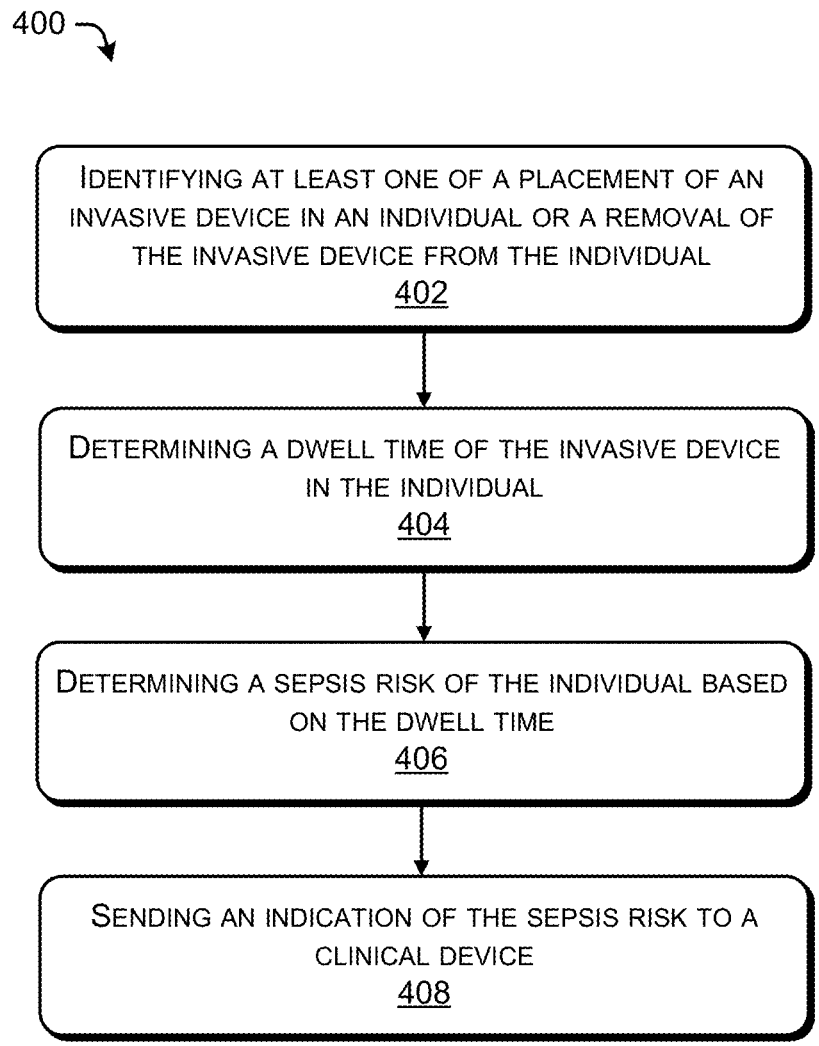
FIG. 4 illustrates an example process for identifying a sepsis risk of an individual based on a dwell time of an invasive device.
Figure 5:
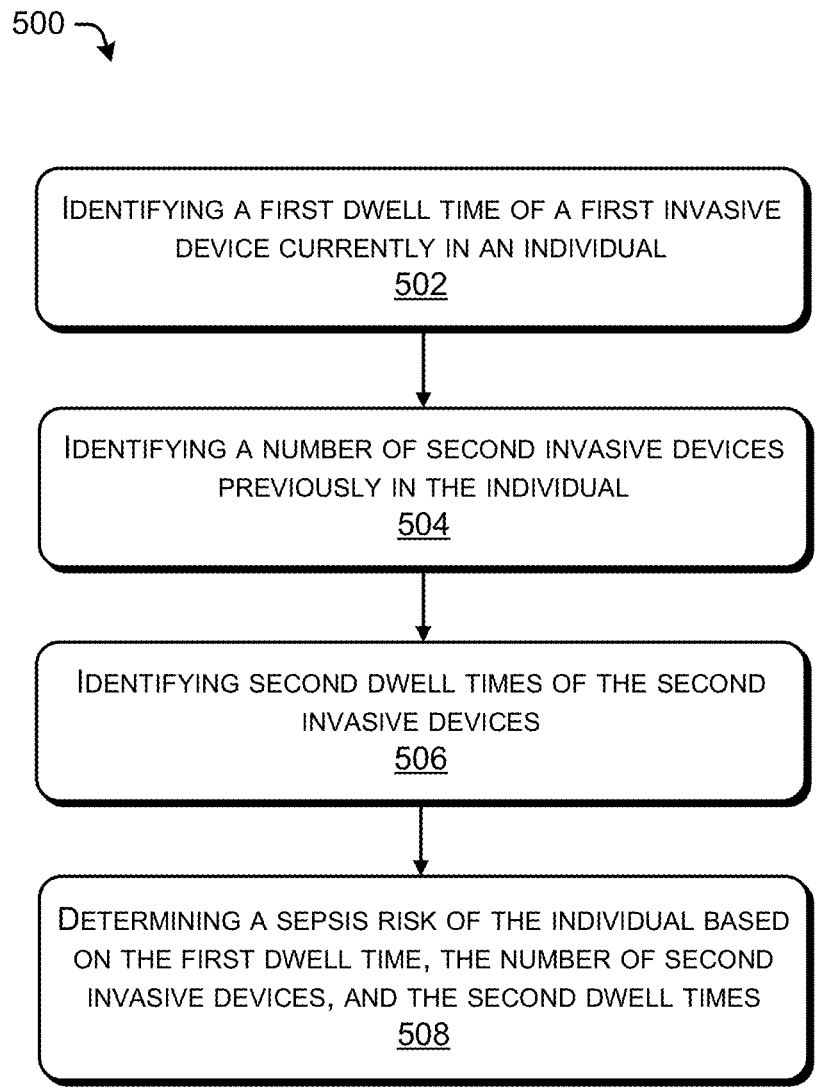
FIG. 5 illustrates an example process for identifying a sepsis risk of an individual based on dwell times of various invasive devices exposed to an individual.
Figure 6:
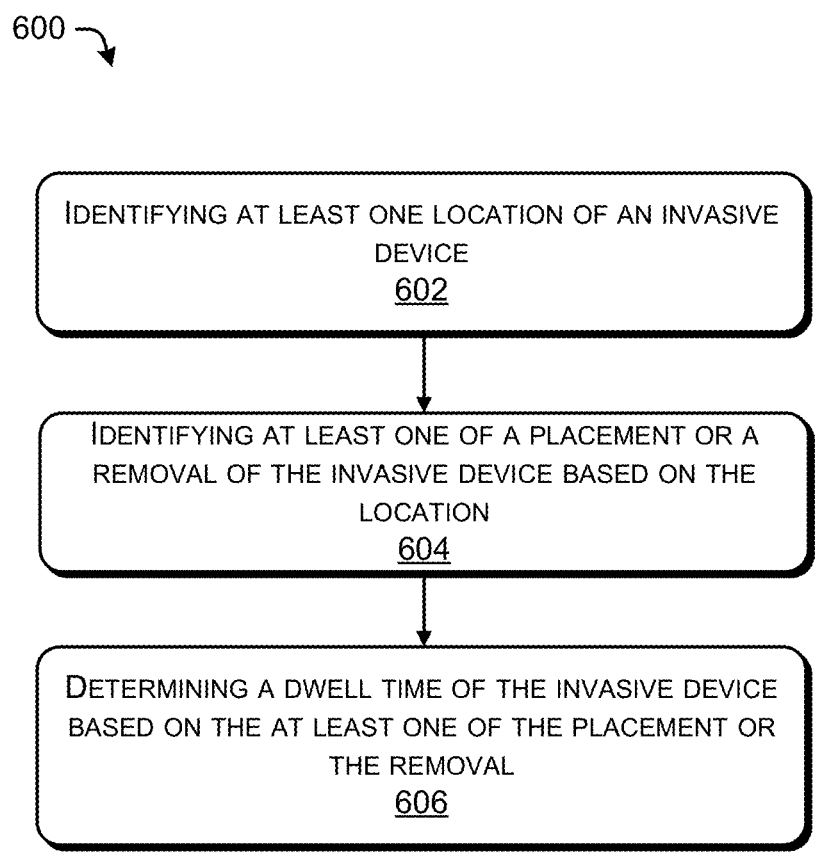
FIG. 6 illustrates an example process for determining a dwell time of an invasive device.

FIGS. 4-6 illustrate processes according to various implementations of the present disclosure. Although FIGS. 4-6 illustrate various example arrangements (e.g., orders of operation) of functions, some implementations include other arrangements of the functions.

FIG. 4 illustrates an example process 400 for identifying a sepsis risk of an individual based on a dwell time of an invasive device. According to various implementations, process 400 may be performed by a sepsis analysis system, such as the sepsis analysis system 110 described above with reference to any of FIGS. 1 to 3.

At 402, the sepsis analysis system may identify at least one of a placement of an invasive device in an individual or a removal of the invasive device from the individual. In some cases, the sepsis analysis system may identify first signals transmitted between a tag attached to the invasive device and multiple transceivers. In some cases, the first signals may identify the individual. For example, the first signals may include and/or indicate an identifier of the tag. In some cases, the sepsis analysis system can use the first signals to derive at least one of an identification (ID) of the individual, a hospital bed utilized by the individual, or a room utilized by the individual. For instance, the sepsis analysis system may identify the location of the tag (and/or the invasive device) based on the first signals. For instance, the sepsis analysis system may perform trilateration, multilateration, or triangulation based on times-of-flight or angles at which the first signals are received by the transceivers.

In some cases, the sepsis analysis system can identify the placement of the invasive device based on the location of the tag. For example, the sepsis analysis system can identify that the invasive device has been placed in the individual by identifying that the location of the tag is within a predetermined distance of a tag associated with the individual. The tag associated with the individual could be attached to the individual (e.g., attached to a bracelet, lanyard, etc. worn by the individual, or another invasive device that has already been placed in the individual), attached to an object (e.g., a hospital bed, a medical device, etc.) associated with the individual, or the like. The location of the tag of the individual could be identified by the sepsis analysis system (e.g., by trilateration, multilateration, or triangulation) based on signals exchanged between the tag and the transceivers. According to certain implementations, the sepsis analysis system can identify that the invasive device has been placed in the individual by determining that the tag is located within a predetermined area (e.g., a hospital room) associated with the individual. In some cases, the sepsis analysis system may identify a time at which the invasive device is placed.

In some example implementations, the sepsis analysis system can identify the removal of the invasive device based on the location of the tag. For instance, the sepsis analysis system can identify that the invasive device has been removed from the individual by identifying that the location of the tag is greater than a predetermined distance from the tag associated with the individual. The predetermined distance used to assess removal can be different from the predetermined distance used to assess placement of the invasive device.

In some cases, the sepsis analysis system can identify that the invasive device has been removed in response to identifying that the location of the tag is within a discard area (e.g., a biological waste container, an autoclave, or the like). In some cases, the discard area can be defined as a static area that does not move. In certain cases, the discard area can be defined as a dynamic area that can move. The dynamic area can be defined according to one or more tags attached to a hollow object, in some cases. One example of a dynamic discard area could be an interior space in a wastebasket (e.g., a sharps container, biohazard disposal box, or the like) that can move throughout a healthcare facility and may be affixed with tags that can be used by the sepsis analysis system to identify the location of the wastebasket. According to certain implementations, the sepsis analysis system can identify the time that the invasive device has been removed.

In some cases, the sepsis analysis system can identify the placement and/or removal of the invasive device based on other types of data. For example, a care provider may log in to a healthcare management computer system and may indicate, in a health record associated with the individual, that the invasive device has been placed and/or removed. The sepsis analysis system may access the health record to identify that the invasive device has been placed and/or removed. The health record may further indicate, to the sepsis analysis system, a time at which the invasive device has been placed and/or a time at which the invasive device has been removed.

At 404, the sepsis analysis system can determine a dwell time of the invasive device in the individual. In some example implementations, the dwell time can be identified as a time interval that begins at the time that the invasive device has been placed. If the invasive device is currently placed, the dwell time can be defined as a time interval between the time at which the invasive device was placed and a current time. On the other hand, if the invasive device has been removed, the dwell time can be defined as a time interval between the time at which the invasive device was placed and the time at which the invasive device was removed.

The sepsis analysis system can determine a sepsis risk of the individual based on the dwell time at 406. In some examples, the sepsis analysis system may store a correlation between sepsis risk and dwell times of particular invasive devices. For instance, the sepsis analysis system may identify that a particular type of the invasive device (e.g., an arterial catheter, an intravenous catheter, a Peripherally Inserted Central Catheter (PICC), a central line, a Foley catheter, a chest tube, a bandage, or a wound dressing) increases the individual's risk for developing sepsis by a particular amount when it is placed in the individual for a certain time. The sepsis analysis system may store an equation that it can use to calculate an increase in sepsis risk for the patient based on variables such as the dwell time. In general, longer dwell times may be associated with increased risks of developing sepsis.

In some cases, the sepsis analysis system may identify the sepsis risk by inputting the dwell time into a trained neural network. The trained neural network may be previously trained based on patient data of a variety of previous patients. The patient data may indicate various information, such as the dwell times of invasive devices placed in the previous patients, whether and how frequently maintenance activities were performed on the invasive devices, whether any of the previous patients developed sepsis, and the like. In some cases, the patient data may include health record information of the previous patients, which may indicate other factors that may correlate to the risks of the previous patients of developing sepsis. For instance, the patient data may include at least one of medical treatments (e.g., whether the patients were administered with antibiotics, whether the patients were administered with immune suppressants, whether the patients were implanted with other devices, etc.), locations (e.g., a geographic area where the patients resided, specific hospitals where the patients were treated, etc.), demographics (e.g., age, socioeconomic status, etc.), diagnoses (e.g., whether the patients were immunocompromised based on diseases, like HIV), or the like. The neural network may be designed to learn from the patient data during a training process, in order to identify correlations between various features of the patient data.

The neural network may be trained by the patient data to output a sepsis risk, or an increase in sepsis risk, associated with the individual based on the dwell time of the invasive device placed in the individual. In some cases, the neural network may also rely on other types of data, such as health record information associated with the individual or information about previous invasive devices placed in the individual, to identify the sepsis risk. According to certain implementations, the neural network may also be trained to identify a recommendation (e.g., a recommended treatment or monitoring plan for the individual) based on the sepsis risk. For instance, if the neural network identifies that the sepsis risk exceeds a threshold (e.g., over 50%), the neural network may identify that the individual should be treated prophylactically with a treatment (e.g., an antibiotic) that is correlated with preventing the development of sepsis. The neural network may identify the correlation between the treatment and the prevention of sepsis based on the patient data.

At 408, the sepsis analysis system may send an indication of the sepsis risk to a clinical device. According to some example implementations, the indication may include, or at least be accompanied by, an identifier of the individual. The identifier could include, for instance, an ID of the individual, a hospital bed utilized by the individual, or a room utilized by the individual. In some cases, by sending the indication of the sepsis risk, the sepsis analysis system may cause the clinical device to output the indication of the sepsis risk and/or the identifier. For example, a screen of the clinical device may display the identifier of the individual along with the individual's sepsis risk. Accordingly, a user of the clinical device (e.g., a nurse, physician, or the like) can develop and/or modify care plans for the individual while accounting for the sepsis risk.

The sepsis analysis system may transmit the indication of the sepsis risk to the clinical device via one or more transceivers. In some cases, the indication can be packaged in the form of one or more data packets. The transceivers may transmit the data packet(s) over a wireless interface (e.g., a Bluetooth interface, a Zigbee interface, a New Radio (NR) interface, or the like). In some cases, the sepsis analysis system may transmit the data packet(s) over a Local Area Network (LAN), a Wide Area Network (WAN) (e.g., the Internet), or the like.

FIG. 5 illustrates an example process 500 for identifying a sepsis risk of an individual based on dwell times of various invasive devices exposed to an individual. According to various implementations, process 500 may be performed by a sepsis analysis system, such as the sepsis analysis system 110 described above with reference to any of FIGS. 1 to 3.

At 502, the sepsis analysis system may identify a first dwell time of a first invasive device currently placed in an individual. In some example implementations, the dwell time can be identified as a time interval that begins at the time that the invasive device has been placed. When the invasive device is currently placed, the dwell time can be defined as a time interval between the time at which the invasive device was placed and a current time.

In some cases, the sepsis analysis system can identify the placement of the invasive device based on the location of a tag attached to the invasive device. For example, the sepsis analysis system can identify that the invasive device has been placed in the individual by identifying that the location of the tag is within a predetermined distance of a tag associated with the individual. The tag associated with the individual could be attached to the individual (e.g., attached to a bracelet, lanyard, etc. worn by the individual, or another invasive device that has already been placed in the individual), attached to an object (e.g., a hospital bed, a medical device, etc.) associated with the individual, or the like. The location of the tag of the individual could be identified by the sepsis analysis system (e.g., by trilateration, multilateration, or triangulation) based on signals exchanged between the tag and the transceivers. According to certain implementations, the sepsis analysis system can identify that the invasive device has been placed in the individual by determining that the tag is located within a predetermined area (e.g., a hospital room) associated with the individual.

In some example implementations, the sepsis analysis system can identify the placement of the invasive device based on other types of data. For example, a care provider may log in to a healthcare management computer system and may indicate, in a health record associated with the individual, that the invasive device has been placed. The sepsis analysis system may access the health record to identify that the invasive device has been placed. The health record may further indicate, to the sepsis analysis system, a time at which the invasive device has been placed.

At 504, the sepsis analysis system may identify a number of second invasive devices previously placed in the individual. In some cases, the sepsis analysis system may access a health record associated with the individual to identify the number of the second invasive devices. According to some example implementations, the sepsis analysis system may receive, from an external system, data indicating the number of second invasive devices that have been placed in the individual. In some examples, the sepsis analysis system may store information about the second invasive devices, which the system can use to identify the number of the second invasive devices.

In certain cases, the second invasive devices may selectively include invasive devices placed in the individual within a particular time period. For example, the second invasive devices may include only invasive devices placed in the individual during a particular hospital stay, invasive devices placed in the individual within a predetermined time period (e.g., the last day, week, month, etc.), or the like. In some examples, the second invasive devices may selectively include invasive devices of a particular type. For instance, the second invasive devices may include only catheters, only bandages, or only some other type of invasive device.

At 506, the sepsis analysis system may identify a number of second dwell times of the second invasive devices. In some cases, the sepsis analysis system may access a health record associated with the individual to identify the dwell times of the second invasive devices. According to some example implementations, the sepsis analysis system may receive, from an external system, data indicating the dwell times of the second invasive devices that have been placed in the individual. In some examples, the sepsis analysis system may store information about the second invasive devices, which the system can use to identify the dwell times of the second invasive devices.

Finally, at 508, the sepsis analysis system can determine a sepsis risk of the individual based on the first dwell time, the number of second invasive devices, and the second dwell times. In some examples, the sepsis analysis system may store a correlation between sepsis risk and dwell times of particular invasive devices. For instance, the sepsis analysis system may identify that a particular type of the invasive device (e.g., an arterial catheter, an intravenous catheter, a Peripherally Inserted Central Catheter (PICC), a central line, a Foley catheter, a chest tube, a bandage, or a wound dressing) increases the individual's risk for developing sepsis by a particular amount when it is placed in the individual for a certain time. In some cases, the sepsis analysis system may identify that a number of invasive devices placed in individuals, dwell times of the invasive devices, frequencies of invasive device placement, or the like, is correlated with effects on sepsis risks of the individuals. The sepsis analysis system may store an equation that it can use to calculate an increase in sepsis risk for the patient based on variables such as the dwell time. In general, longer dwell times and exposure to a greater number of invasive devices may be associated with increased risks of developing sepsis.

In some cases, the sepsis analysis system may identify the sepsis risk by inputting the current dwell time of the first invasive device, the number of second invasive devices, and/or the dwell times of the second invasive devices into a trained neural network. The trained neural network may be previously trained based on patient data of a variety of previous patients. The patient data may indicate various information, such as the dwell times of invasive devices placed in the previous patients, whether any of the previous patients developed sepsis, and the like. In some cases, the patient data may include health record information of the previous patients, which may indicate other factors that may correlate to the risks of the previous patients of developing sepsis. For instance, the patient data may include at least one of medical treatments (e.g., whether the patients were administered with antibiotics, whether the patients were administered with immune suppressants, whether the patients were implanted with other devices, etc.), locations (e.g., a geographic area where the patients resided, specific hospitals where the patients were treated, etc.), demographics (e.g., age, socioeconomic status, etc.), diagnoses (e.g., whether the patients were immunocompromised based on diseases, like HIV), or the like. The neural network may be designed to learn from the patient data during a training process, in order to identify correlations between various features of the patient data.

The neural network may be trained by the patient data to output a sepsis risk, or an increase in sepsis risk, associated with the individual based on the current dwell time of the first invasive device, the number of second invasive devices previously placed in the individual, and/or the dwell times of the second invasive devices. In some cases, the neural network may also rely on other types of data, such as health record information associated with the individual, to identify the sepsis risk. According to certain implementations, the neural network may also be trained to identify a recommendation (e.g., a recommended treatment or monitoring plan for the individual) based on the sepsis risk. For instance, if the neural network identifies that the sepsis risk exceeds a threshold (e.g., over 50%), the neural network may identify that the individual should be treated prophylactically with a treatment (e.g., an antibiotic) that is correlated with preventing the development of sepsis. The neural network may identify the correlation between the treatment and the prevention of sepsis based on the patient data.

FIG. 6 illustrates an example process 600 for determining a dwell time of an invasive device. According to various implementations, process 600 may be performed by a sepsis analysis system, such as the sepsis analysis system 110 described above with reference to any of FIGS. 1 to 3.

At 602, the sepsis analysis system may identify at least one location of an invasive device. In some cases, the sepsis analysis system may identify first signals transmitted between a tag attached to the invasive device and multiple transceivers. In some cases, the first signals may include and/or indicate an identifier of the tag. In some cases, the sepsis analysis system can identify the individual based on the first signals. For example, the first signals may include and/or indicate at least one of an identification (ID) of the individual, a hospital bed utilized by the individual, or a room utilized by the individual. The sepsis analysis system may identify the location of the tag (and/or the invasive device) based on the first signals. For instance, the sepsis analysis system may perform trilateration, multilateration, or triangulation based on times-of-flight or angles at which the first signals are received by the transceivers.

At 604, the sepsis analysis system may identify at least one of a placement or a removal of the invasive device based on the location. For example, the sepsis analysis system can identify that the invasive device has been placed in the individual by identifying that the location of the tag is within a predetermined distance of a tag associated with the individual. The tag associated with the individual could be attached to the individual (e.g., attached to a bracelet, lanyard, etc. worn by the individual, or another invasive device that has already been placed in the individual), attached to an object (e.g., a hospital bed, a medical device, etc.) associated with the individual, or the like. The location of the tag of the individual could be identified by the sepsis analysis system (e.g., by trilateration, multilateration, or triangulation) based on signals exchanged between the tag and the transceivers. According to certain implementations, the sepsis analysis system can identify that the invasive device has been placed in the individual by determining that the tag is located within a predetermined area (e.g., a hospital room) associated with the individual. In some cases, the sepsis analysis system may identify a time at which the invasive device is placed.

In some example implementations, the sepsis analysis system can identify the removal of the invasive device based on the location of the tag. For instance, the sepsis analysis system can identify that the invasive device has been removed from the individual by identifying that the location of the tag is greater than a predetermined distance from the tag associated with the individual. The predetermined distance used to assess removal can be different from the predetermined distance used to assess placement of the invasive device.

In some cases, the sepsis analysis system can identify that the invasive device has been removed in response to identifying that the location of the tag is within a discard area (e.g., a biological waste container, an autoclave, or the like). In some cases, the discard area can be defined as a static area that does not move. In certain cases, the discard area can be defined as a dynamic area that can move. The dynamic area can be defined according to one or more tags attached to a hollow object, in some cases. One example of a dynamic discard area could be an interior space in a wastebasket (e.g., a sharps container, biohazard disposal box, or the like) that can move throughout a healthcare facility and may be affixed with tags that can be used by the sepsis analysis system to identify the location of the wastebasket. According to certain implementations, the sepsis analysis system can identify the time that the invasive device has been removed.

In some cases, the sepsis analysis system can identify the placement and/or removal of the invasive device based on other types of data in combination with the location of the tag. For example, a care provider may log in to a healthcare management computer system and may indicate, in a health record associated with the individual, that the invasive device has been placed and/or removed. The sepsis analysis system may access the health record to identify that the invasive device has been placed and/or removed. The health record may further indicate, to the sepsis analysis system, a time at which the invasive device has been placed and/or a time at which the invasive device has been removed.

At 606, the sepsis analysis system may determine a dwell time of the invasive device based on the placement and/or the removal determined at 604. In some example implementations, the dwell time can be identified as a time interval that begins at the time that the invasive device has been placed. If the invasive device is currently placed, the dwell time can be defined as a time interval between the time at which the invasive device was placed and a current time. On the other hand, if the invasive device has been removed, the dwell time can be defined as a time interval between the time at which the invasive device was placed and the time at which the invasive device was removed.

Figure 7:
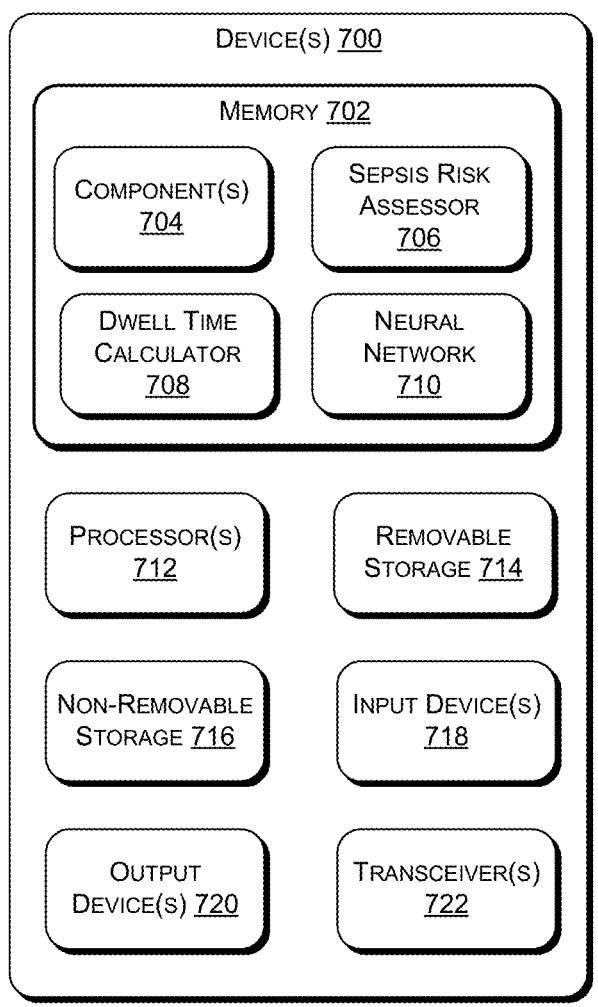
FIG. 7 illustrates at least one example device that can carry out various functionality described herein.

FIG. 7 illustrates an example system including at least one device 700. In some example implementations, the system illustrated in FIG. 7 may perform any of the functionality described herein. The device(s) 700 may be implemented by at least one of server computer(s), dedicated hardware, software operating on dedicated hardware, or virtualized function(s) hosted on an appropriate platform (e.g., cloud infrastructure). The device(s) 700 may be implemented as a single device or as multiple devices with components and data distributed among them.

As illustrated, the device(s) 700 comprise a memory 702. In various implementations, the memory 702 is volatile (such as Random Access Memory (RAM)), non-volatile (such as Read Only Memory (ROM), flash memory, etc.) or some combination of the two. Various elements stored in the memory 702 can include methods, threads, processes, applications, objects, modules, or any other sort of executable instructions. Elements stored in the memory 702 may be non-transitory. The memory 702 may also store various files, databases, or the like.

The memory 702 may include various components 704, which can be executed by processor(s) 712 to perform any of the functionality described herein. The memory 702 may include a sepsis risk assessor 706, which, when executed by the processor(s) 712, may cause the processor(s) 712 to perform various functionality associated with determining a sepsis risk. The memory 702 may include a dwell time calculator 708, which, when executed by the processor(s) 712, may cause the processor(s) 712 to perform various functionality associated with determining a dwell time. The memory 702 may, in some cases, include a neural network 710 that may be trained so that when it is executed by the processor(s) 712, the processor(s) 712 may identify a sepsis risk, a recommendation, or the like. In some implementations, the processor(s) 712 includes a Central Processing Unit (CPU), a Graphics Processing Unit (GPU), or both CPU and GPU, or other processing unit or component known in the art.

The device(s) 700 can also include additional data storage components such as, for example, magnetic disks, optical disks, or tape. These additional data storage components can include removable storage 714 and non-removable storage 716. Tangible computer-readable media can include volatile and nonvolatile, removable and non-removable media implemented in any method or technology for storage of information, such as computer readable instructions, data structures, program modules, or other data.

The memory 702, removable storage 714, and non-removable storage 716 can all be examples of computer-readable storage media. Computer-readable storage media include, but are not limited to, RAM, ROM, EEPROM, flash memory or other memory technology, CD-ROM, Digital Versatile Discs (DVDs), Content-Addressable Memory (CAM), or other optical storage, magnetic cassettes, magnetic tape, magnetic disk storage or other magnetic storage devices, or any other medium which can be used to store the desired information and which can be accessed by the device(s) 700. Any such tangible computer-readable media can be part of the device(s) 700.

The device(s) 700 can also include input device(s) 912 and output device(s) 720. In some implementations, the input device(s) 718 can include at least one of a keypad, a cursor control, a touch-sensitive display, a voice input device, a haptic feedback device, or the like. The output device(s) 720 can include at least one of a display, speakers, a haptic output device, printers, etc. These devices are well known in the art and need not be discussed at length here.

As illustrated in FIG. 7, the device(s) 700 can also include one or more wired or wireless transceiver(s) 722. For example, the transceiver(s) 722 can include a Network Interface Card (NIC), a network adapter, a Local Area Network (LAN) adapter, or a physical, virtual, or logical address to connect to the various external devices and/or systems. The transceiver(s) 722 can include any sort of wireless transceivers capable of engaging in wireless communication (e.g., Radio Frequency (RF) communication). The transceiver(s) 722 can also include other wireless modems, such as a modem for engaging in Wi-Fi, WiMAX, Bluetooth, or infrared communication.

The following clauses describe one or more example embodiments of the present disclosure, either alone or in combination.

A. A system including: a tag configured to attach to an invasive device and to transmit first signals; a plurality of transceivers configured to receive the first signals; and a server operably connected to the transceiver, the server including: a processor; and memory storing instructions that, when executed by the processor, cause the processor to perform operations including: identifying, based on the first signals, a placement of the invasive device in an individual; determining a dwell time of the invasive device in the individual based on the placement of the invasive device; determining, based on the dwell time, a sepsis risk associated with the individual; and generating a second signal indicating the sepsis risk associated with the individual.

B. The system of clause A, wherein the operations further include: identifying a location of the tag based on the first signals, the placement of the invasive device being identified based on the location of the tag.

C. The system of clause B, wherein the operations further include: identifying removal of the invasive device from the individual by determining an additional location of the tag within a predetermined discard area.

D. The system of clause C, wherein the dwell time includes a time interval extending from the placement of the invasive device to the removal of the invasive device.

E. The system of any one of clauses B to D, the tag being a first tag, wherein identifying the placement of the invasive device comprises determining that the location of the first tag is within a predetermined distance of a location of a second tag associated with the individual or within a predetermined area associated with the individual.

F. The system of any one of clauses A to E, wherein the invasive device includes at least one of an arterial catheter, an intravenous catheter, a Peripherally Inserted Central Catheter (PICC), a central line, a Foley catheter, a chest tube, a bandage, or a wound dressing.

G. The system of any one of clauses A to F, wherein the operations further include: identifying, based on the first signals, at least one of an identification (ID) of the individual, a hospital bed utilized by the individual, or a room utilized by the individual, and wherein the second signal indicates at least one of the ID of the individual, the hospital bed utilized by the individual, or the room utilized by the individual.

H. The system of any one of clauses A to G, wherein the invasive device includes a first invasive device and the dwell time includes a first dwell time, the operations further including: accessing a health record associated with the individual; identifying, based on the health record, a number of one or more second invasive devices placed in the individual within a predetermined time; and identifying, based on the health record, one or more second dwell times of the one or more second invasive devices, wherein the sepsis risk is determined based on the number of the one or more second invasive devices and the one or more second dwell times.

I. The system of any one of clauses A to H, wherein determining the sepsis risk includes: inputting the dwell time into a trained neural network, the trained neural network being trained based on patient data indicating dwell times of invasive devices placed in patients and sepsis outcomes of the patients; and receiving the sepsis risk from the trained neural network.

J. The system of any one of clauses A to I, wherein sending the second signal includes causing the electronic device to output a recommendation associated with care of the individual based on the sepsis risk, and wherein the recommendation includes at least one of a recommended dwell time limit for a second invasive device to be placed in the individual, a recommended prophylactic treatment to administer to the individual, a recommendation to remove the invasive device at a particular time, or a recommended monitoring schedule associated with the individual.

K. An apparatus, including: at least one processor; and memory storing instructions that, when executed by the at least one processor, cause the at least one processor to perform operations including: identifying, based on first signals exchanged between a tag attached to an invasive device and multiple transceivers, a location of the tag; determining a dwell time of the invasive device in an individual based on the location of the tag; determining a sepsis risk associated with the individual based on the dwell time; and generating a second signal indicating the sepsis risk associated with the individual.

L. The apparatus of clause K, wherein determining the dwell time includes: identifying, based on the location of the tag, a first time at which the invasive device is inserted into the individual; identifying, based on the location of the tag, a second time at which the invasive device is removed from the individual; and determining a time interval extending from the first time to the second time.

M. The apparatus of clause L, the tag being a first tag, wherein identifying the first time includes identifying a time at which the location of the first tag is within a predetermined distance of a second tag associated with the individual, and wherein identifying the second time comprises determining a time at which the location of the first tag enters a predetermined discard area.

N. The apparatus of any one of clauses K to M, the invasive device being a first invasive device, wherein the operations further include: accessing a health record associated with the individual; identifying, based on the health record, a number of one or more second invasive devices previously placed in the individual within a predetermined time; and identifying, based on the health record, one or more second dwell times of the one or more second invasive devices, wherein the sepsis risk is determined based on the number of the one or more second invasive devices and the one or more second dwell times.

O. The apparatus of any one of clauses K to N, wherein determining the sepsis risk includes: inputting the dwell time into a trained neural network, the trained neural network being trained based on patient data indicating dwell times of invasive devices placed in patients and sepsis outcomes of the patients; and receiving the sepsis risk from the trained neural network.

P. A method, including receiving, from multiple transceivers, location data indicating first signals transmitted between the multiple transceivers and a tag attached to an invasive device; identifying, based on the location data, a location of the invasive device; determining a dwell time of the invasive device in the individual based on the location; determining a sepsis risk associated with the individual based on the dwell time; and generating a second signal indicating the sepsis risk associated with the individual.

Q. The method of clause P, the tag being a first tag, wherein identifying the dwell time includes: identifying a first time when the location is within a predetermined distance of a tag associated with an individual or within a predetermined area associated with the individual; identifying a second time when the location is within a predetermined discard area; and identifying the dwell time as a time interval between the first time and the second time.

R. The method of clause P or Q, the invasive device being a first invasive device, the method further including: accessing a health record associated with the individual; identifying, based on the health record, a number of one or more second invasive devices previously placed in the individual within a predetermined time; and identifying, based on the health record, one or more second dwell times of the one or more second invasive devices, and wherein the sepsis risk is determined based on the number of the one or more second invasive devices and the one or more second dwell times.

S. The method of any one of clauses P to R, further including: training a neural network using patient data indicating dwell times of invasive devices placed in patients and sepsis outcomes of the patients; inputting the dwell time into the neural network; and in response to inputting the dwell time into the neural network, receiving the sepsis risk from the trained neural network.

T. The method of any one of clauses P to S, the invasive device being a first invasive device, the method further including: identifying a recommendation based on the sepsis risk, the recommendation including at least one of a recommended dwell time limit for a second invasive device to be placed in the individual, a recommended prophylactic treatment to administer to the individual, a recommendation to remove the invasive device at a particular time, or a recommended monitoring schedule associated with the individual; and sending, to the clinical device, the recommendation.

In some instances, one or more components may be referred to herein as "configured to," "configurable to," "operable/operative to," "adapted/adaptable," "able to," "conformable/conformed to," etc. Those skilled in the art will recognize that such terms (e.g., "configured to") can generally encompass active-state components and/or inactive-state components and/or standby-state components, unless context requires otherwise.

As used herein, the term "based on" can be used synonymously with "based, at least in part, on" and "based at least partly on."

As used herein, the terms "comprises/comprising/comprised" and "includes/including/included," and their equivalents, can be used interchangeably. An apparatus, system, or method that "comprises A, B, and C" includes A, B, and C, but also can include other components (e.g., D) as well. That is, the apparatus, system, or method is not limited to components A, B, and C.

Although the subject matter has been described in language specific to structural features and/or methodological acts, it is to be understood that the subject matter defined in the appended claims is not necessarily limited to the specific features or acts described.

The invention claimed is:

1. A system, comprising:
    a tag configured to attach to an invasive device and to transmit first signals;
    a plurality of transceivers configured to receive the first signals; and
    a server operably connected to the transceiver, the server comprising:
        a processor; and
        memory storing instructions that, when executed by the processor, cause the processor to perform operations comprising:
            identifying, based on the first signals, a placement of the invasive device in an individual;
            determining a dwell time of the invasive device in the individual based on the placement of the invasive device;
            determining, based on the dwell time, a sepsis risk associated with the individual; and
            generating a second signal indicating the sepsis risk associated with the individual.

2. The system of claim 1, wherein the operations further comprise:
    identifying a location of the tag based on the first signals, the placement of the invasive device being identified based on the location of the tag.

3. The system of claim 2, wherein the operations further comprise:
    identifying removal of the invasive device from the individual by determining that an additional location of the tag is within a predetermined discard area.

4. The system of claim 3, wherein the dwell time comprises a time interval extending from the placement of the invasive device to the removal of the invasive device.

5. The system of claim 2, the tag being a first tag, wherein identifying the placement of the invasive device comprises determining that the location of the first tag is within a predetermined distance of a location of a second tag associated with the individual or is within a predetermined area associated with the individual.

6. The system of claim 1, wherein the invasive device comprises at least one of an arterial catheter, an intravenous catheter, a Peripherally Inserted Central Catheter (PICC), a central line, a Foley catheter, a chest tube, a bandage, or a wound dressing.

7. The system of claim 1, wherein the operations further comprise:
    identifying, based on the first signals, at least one of an identification (ID) of the individual, a hospital bed utilized by the individual, or a room utilized by the individual, and
    wherein the second signal indicates at least one of the ID of the individual, the hospital bed utilized by the individual, or the room utilized by the individual.

8. The system of claim 1, wherein the invasive device comprises a first invasive device and the dwell time comprises a first dwell time, the operations further comprising:
    accessing a health record associated with the individual;
    identifying, based on the health record, a number of one or more second invasive devices placed in the individual within a predetermined time; and
    identifying, based on the health record, one or more second dwell times of the one or more second invasive devices, and
    wherein the sepsis risk is determined based on the number of the one or more second invasive devices and the one or more second dwell times.

9. The system of claim 1, wherein determining the sepsis risk comprises:
    inputting the dwell time into a trained neural network, the trained neural network being trained based on patient data indicating dwell times of invasive devices placed in patients and sepsis outcomes of the patients; and
    receiving the sepsis risk from the trained neural network.

10. The system of claim 1, wherein sending the second signal comprises causing the electronic device to output a recommendation associated with care of the individual based on the sepsis risk, and
    wherein the recommendation comprises at least one of a recommended dwell time limit for a second invasive device to be placed in the individual, a recommended prophylactic treatment to administer to the individual, a recommendation to remove the invasive device at a particular time, or a recommended monitoring schedule associated with the individual.

11. An apparatus, comprising:
    at least one processor; and
    memory storing instructions that, when executed by the at least one processor, cause the at least one processor to perform operations comprising:
        identifying, based on first signals exchanged between a tag attached to an invasive device and multiple transceivers, a location of the tag;
        determining a dwell time of the invasive device in an individual based on the location of the tag;
        determining a sepsis risk associated with the individual based on the dwell time; and
        generating a second signal indicating the sepsis risk associated with the individual.

12. The apparatus of claim 11, wherein determining the dwell time comprises:
    identifying, based on the location of the tag, a first time at which the invasive device is inserted into the individual;
    identifying, based on the location of the tag, a second time at which the invasive device is removed from the individual; and
    determining a time interval extending from the first time to the second time.

13. The apparatus of claim 12, the tag being a first tag, wherein identifying the first time comprises identifying a time at which the location of the first tag is within a predetermined distance of a second tag associated with the individual, and
    wherein identifying the second time comprises determining a time at which the location of the first tag enters a predetermined discard area.

14. The apparatus of claim 11, the invasive device being a first invasive device, wherein the operations further comprise:
- accessing a health record associated with the individual;
- identifying, based on the health record, a number of one or more second invasive devices previously placed in the individual within a predetermined time; and
- identifying, based on the health record, one or more second dwell times of the one or more second invasive devices, and
- wherein the sepsis risk is determined based on the number of the one or more second invasive devices and the one or more second dwell times.

15. The apparatus of claim 11, wherein determining the sepsis risk comprises:
- inputting the dwell time into a trained neural network, the trained neural network being trained based on patient data indicating dwell times of invasive devices placed in patients and sepsis outcomes of the patients; and
- receiving the sepsis risk from the trained neural network.

16. A method, comprising:
- receiving, from multiple transceivers, location data indicating first signals transmitted between the multiple transceivers and a tag attached to an invasive device;
- identifying, based on the location data, a location of the invasive device;
- determining a dwell time of the invasive device in the individual based on the location;
- determining a sepsis risk associated with the individual based on the dwell time; and
- generating a second signal indicating the sepsis risk associated with the individual.

17. The method of claim 16, the tag being a first tag, wherein identifying the dwell time comprises:
- identifying a first time when the location is within a predetermined distance of a tag associated with an individual or within a predetermined area associated with the individual;
- identifying a second time when the location is within a predetermined discard area; and
- identifying the dwell time as a time interval between the first time and the second time.

18. The method of claim 16, the invasive device being a first invasive device, the method further comprising:
- accessing a health record associated with the individual;
- identifying, based on the health record, a number of one or more second invasive devices previously placed in the individual within a predetermined time; and
- identifying, based on the health record, one or more second dwell times of the one or more second invasive devices, and
- wherein the sepsis risk is determined based on the number of the one or more second invasive devices and the one or more second dwell times.

19. The method of claim 16, further comprising:
- training a neural network using patient data indicating dwell times of invasive devices placed in patients and sepsis outcomes of the patients;
- inputting the dwell time into the neural network; and
- in response to inputting the dwell time into the neural network, receiving the sepsis risk from the trained neural network.

20. The method of claim 16, the invasive device being a first invasive device, the method further comprising:
- identifying a recommendation based on the sepsis risk, the recommendation comprising at least one of a recommended dwell time limit for a second invasive device to be placed in the individual, a recommended prophylactic treatment to administer to the individual, a recommendation to remove the invasive device at a particular time, or a recommended monitoring schedule associated with the individual; and
- sending, to the clinical device, the recommendation.

* * * * *